United States Patent
Nishioka

(10) Patent No.: US 6,635,288 B2
(45) Date of Patent: Oct. 21, 2003

(54) COMPOSITION FOR SUPPRESSING CELLULAR FIBROUSING AND METHOD FOR PREPARING AN EXTRACT FROM LOQUAT SEEDS

(75) Inventor: Yutaka Nishioka, Nankoku (JP)

(73) Assignee: Kochi Medical School, Nankoku (JP)

(*) Notice: Subject to any disclaimer, the term of this patent is extended or adjusted under 35 U.S.C. 154(b) by 0 days.

(21) Appl. No.: 09/796,360

(22) Filed: Mar. 2, 2001

(65) Prior Publication Data

US 2001/0028899 A1 Oct. 11, 2001

(30) Foreign Application Priority Data

Mar. 2, 2000 (JP) .......................... 2000-56884

(51) Int. Cl.⁷ .............................. A61K 35/78
(52) U.S. Cl. ...................... 424/776; 424/725
(58) Field of Search .................. 424/725, 776

(56) References Cited

U.S. PATENT DOCUMENTS

2001/0009903 A1 * 7/2001 Niwa

FOREIGN PATENT DOCUMENTS

| JP | 62263113 | * | 11/1987 |
| JP | 06227998 | * | 8/1994 |
| JP | 06-227998 | | 8/1994 |
| JP | 6227998 | * | 8/1994 |
| WO | WO97/066559 | | 2/1997 |

OTHER PUBLICATIONS

Hamada et al. Yukagaku. 1967. vol. 16, No. 12, pp. 677–680, Caplus Abstract enclosed.*
Raie et al. Fette Seifen Anstrichm. 1983. vol. 8, pp. 325–326, Biotechds Abstract enclosed.*
G. Lotti et al, "Sulla composizione di nuovi olii di semi", Agrochimica, vol. 35, No. 1–2–3, pp. 58–68, XP000999525 Jan.–Jun. 1991.

* cited by examiner

Primary Examiner—Christopher R. Tate
(74) Attorney, Agent, or Firm—Burns, Doane, Swecker & Mathis, LLP

(57) ABSTRACT

A composition containing an extract from loquat seeds which is effective for suppressing cellular fibrousing. The composition is based on an extract from loquat seeds which can be obtained by immersing grains obtained by pulverizing loquat seeds, immersing them in at least one solvent selected from a group comprising ethanol, methanol, water and hexane, and separating a supernatant therefrom.

1 Claim, 6 Drawing Sheets

Mobile phase : chloroform : methanol : water = 8 : 2 : 0.2
Conditions : after spraying 10% sulfuric scid, heating, UV radiation
Thin plate : silicagel 60 F254

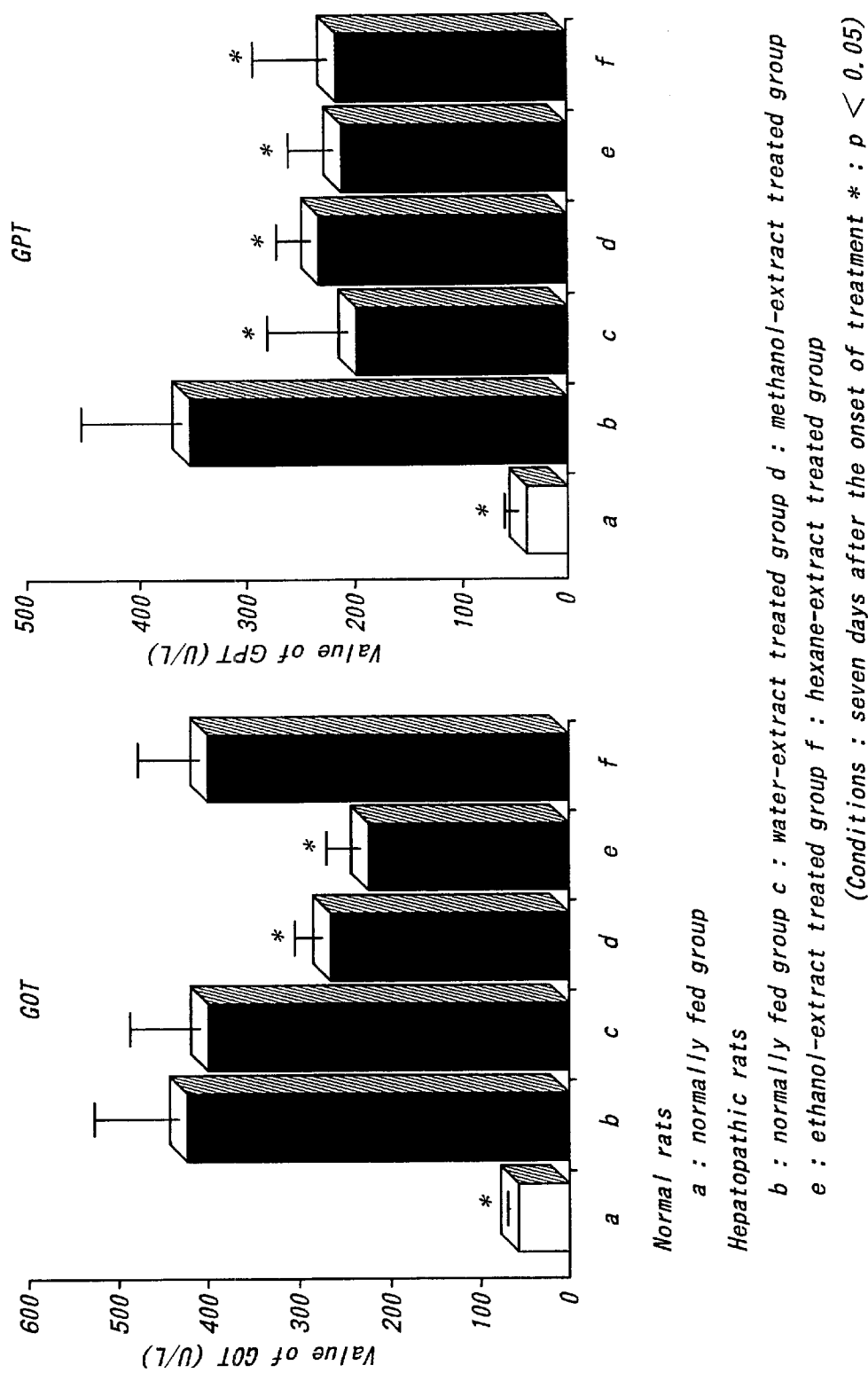

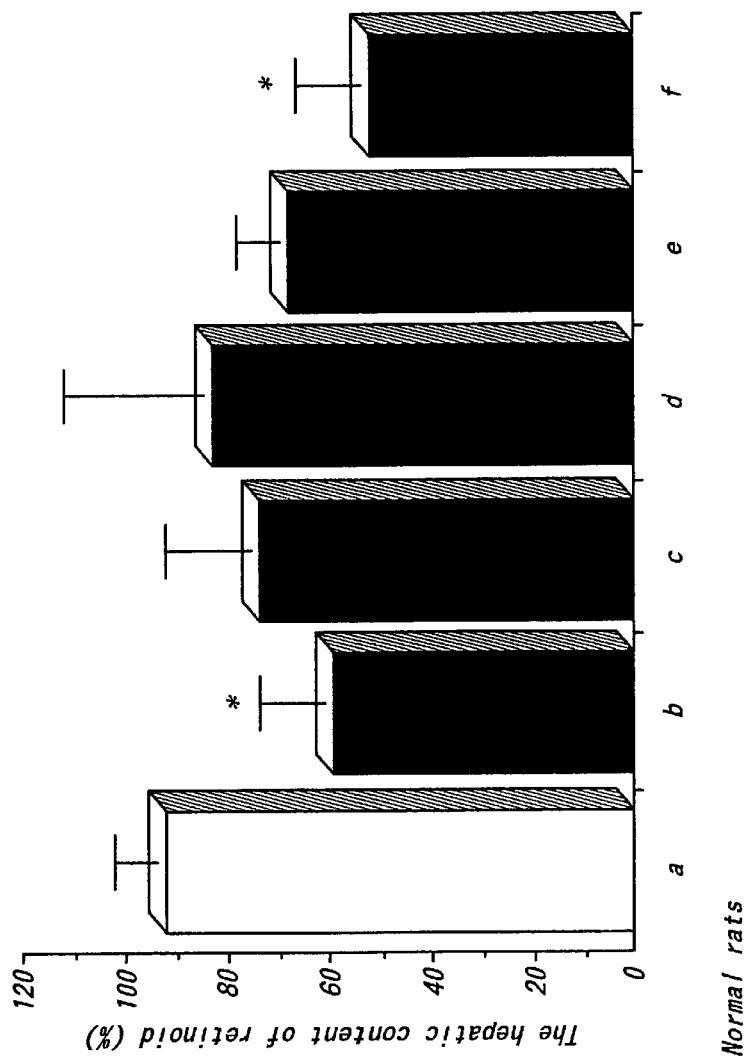

FIG. 4

Normal rats
a : normally fed group

Hepatopathic rats
b : normally fed group  c : water-extract treated group  d : methanol-extract treated group
e : ethanol-extract treated group  f : hexane-extract treated group (Conditions : seven days after the onset of treatment * : p < 0.05)

The hepatic retinoid content is expressed as a percentage relative to the value obtained 7 days after the preliminary feeding

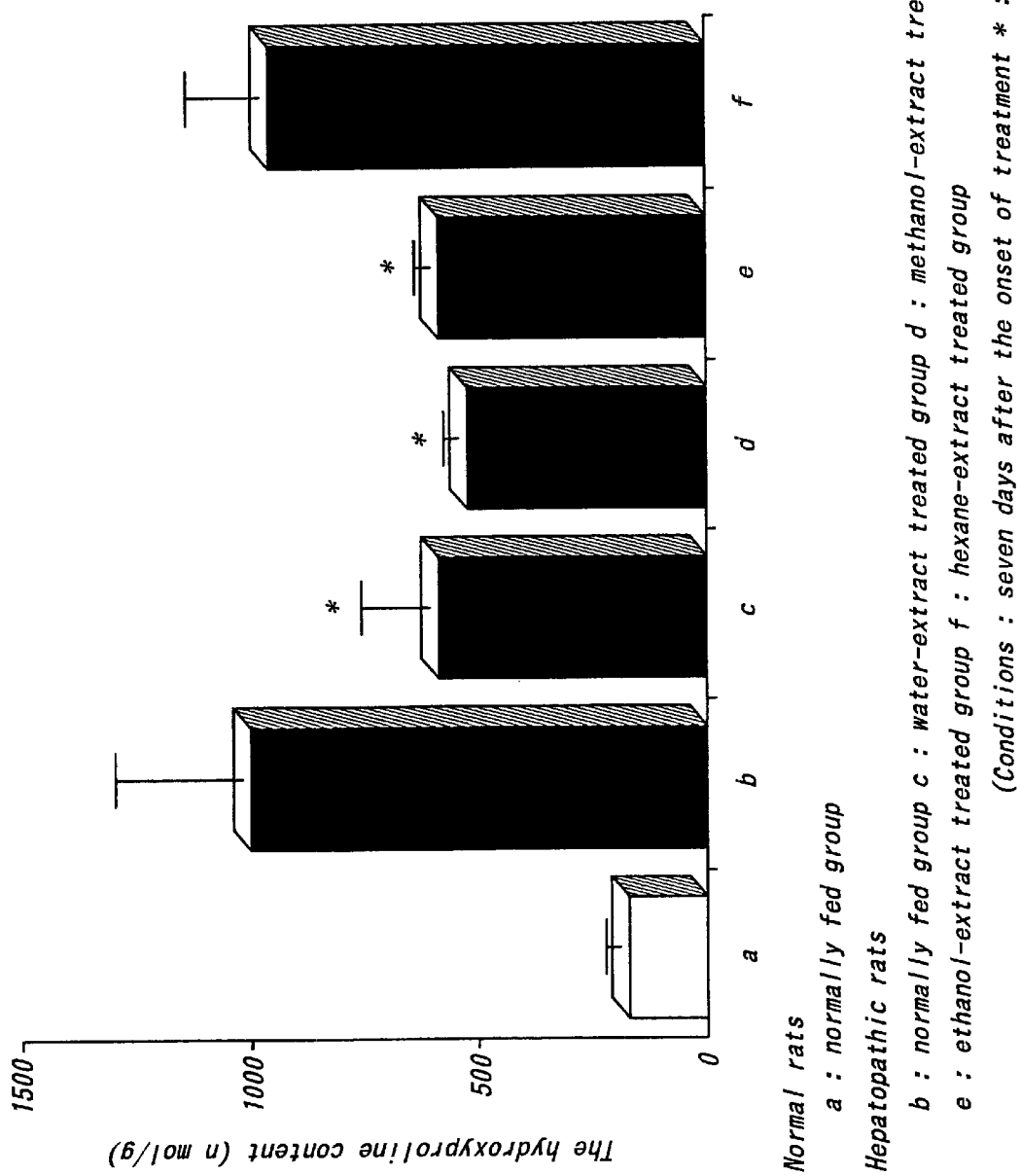

b : normally fed group  c : water-extract treated group  d : methanol-extract treated group
e : ethanol-extract treated group  f : hexane-extract treated group (Conditions : seven days after the onset of treatment  * : p < 0.05)

The cellular fiber deposition is expressed as a percentage relative to the value from hepatopathic rats on normal feed

COMPOSITION FOR SUPPRESSING CELLULAR FIBROUSING AND METHOD FOR PREPARING AN EXTRACT FROM LOQUAT SEEDS

BACKGROUND OF THE INVENTION

1. Field of the Invention

The present invention relates to a composition to suppress cellular fibrousing, particularly to a composition adapted to suppress cellular fibrousing and containing an extract from loquat seeds.

2. Prior Art

It has been revealed recently that fibrousing is deeply involved in the cells of various organs such as liver, lungs, kidneys, etc., and general cells of the skin with respect to the development of intractable diseases of those organs such as chronic hepatitis, hepatic cirrhosis, interstitial pneumonitis, glomerulosclerosis, and hidebound disease. Cellular fibrousing refers to an increase in a fibrous component at a local site within the tissue of an organ, and the condition in which fibrousing is confined not to the local site but spreads widely in the organ is called fibrosis. It has been revealed that fibrousing by hepatocytes as a result of chronic hepatitis may often lead to the development of hepatic cirrhosis and hepatic cancer. Thus, it has been regarded important to find how to suppress the fibrousing of hepatocytes, thereby preventing the development of hepatic cirrhosis and hepatic cancer. To achieve this, studies have been made to screen medicines possibly effective for suppressing the fibrousing of hepatocytes, and to investigate their effects and action mechanisms.

However, although some candidate suppressants have been found, the mechanism by which they suppress cellular fibrousing is not yet fully clarified. Therefore, if it were possible to elucidate the mechanism responsible for their suppression effects against fibrousing, and to reproduce the mechanism by some means, the knowledge would be immensely valuable in the treatment of various intractable diseases involved in fibrousing.

SUMMARY OF THE INVENTION

In view of this, the present invention aims at providing a composition useful for suppressing cellular fibrousing.

And now, loquat is widely cultivated in Japan as a fruit tree. Its fruits are used as food, and its leaves are used as a loquat leaf medicine for curing skin diseases, and as an anti-inflammatory and pain-killer. However, its seeds are simply discarded as waste and have never been used for any useful purpose.

The present inventors studied extracts from seeds of various plants. They particularly studied the suppression effect of the extracts from loquat seeds on cellular fibrousing, and succeeded in finding the composition of this invention.

The composition of the present invention is characterized by containing an extract from loquat seeds.

The extract is obtained from the loquat seeds by pulverizing loquat seeds, immersing the pulverized material in at least one solvent selected from the group consisting of ethanol, methanol, water and hexane, and separating the supernatant.

The method for preparing a loquat seed extract according to this invention comprises the steps of pulverizing loquat seeds, immersing the grain in a solvent, and separating the supernatant.

The method for preparing a loquat seed extract in this invention, at least one selected from the group comprising ethanol, methanol, water and hexane is used as a solvent.

BRIEF DESCRIPTION OF THE DRAWINGS

FIG. 3 shows results of biochemical tests (GOT, GPT) performed on rats treated with various loquat seed extracts obtained by means of different solvents;

FIG. 4 shows the effect of various loquat seed extracts obtained by means of different solvents on the retinoid content of the liver of rats;

FIG. 5 shows the effect of various loquat seed extracts obtained by means of different solvents on the hydroxyproline content of the liver of rats.

DETAILED DESCRIPTION OF THE INVENTION

The composition of the present invention contains an extract from loquat seeds. This extract is derived from loquat seeds. The loquat seed extract used in this invention includes all the extracts from loquat seeds.

The cells to which the composition of this invention may be applied are not limited to any specific cells, but may include, for example, the cells of internal organs such as liver, lungs, kidneys, etc., and the cells of the general bodily systems such as skin. The cells to which the composition of this invention is particularly effective include hepatocytes, and hence this invention will be described with an emphasis on hepatocytes, but this does not imply that use of the composition of this invention is intended to be limited only to hepatocytes.

Preparation of an Extract from Loquat Seeds

Figure 1:
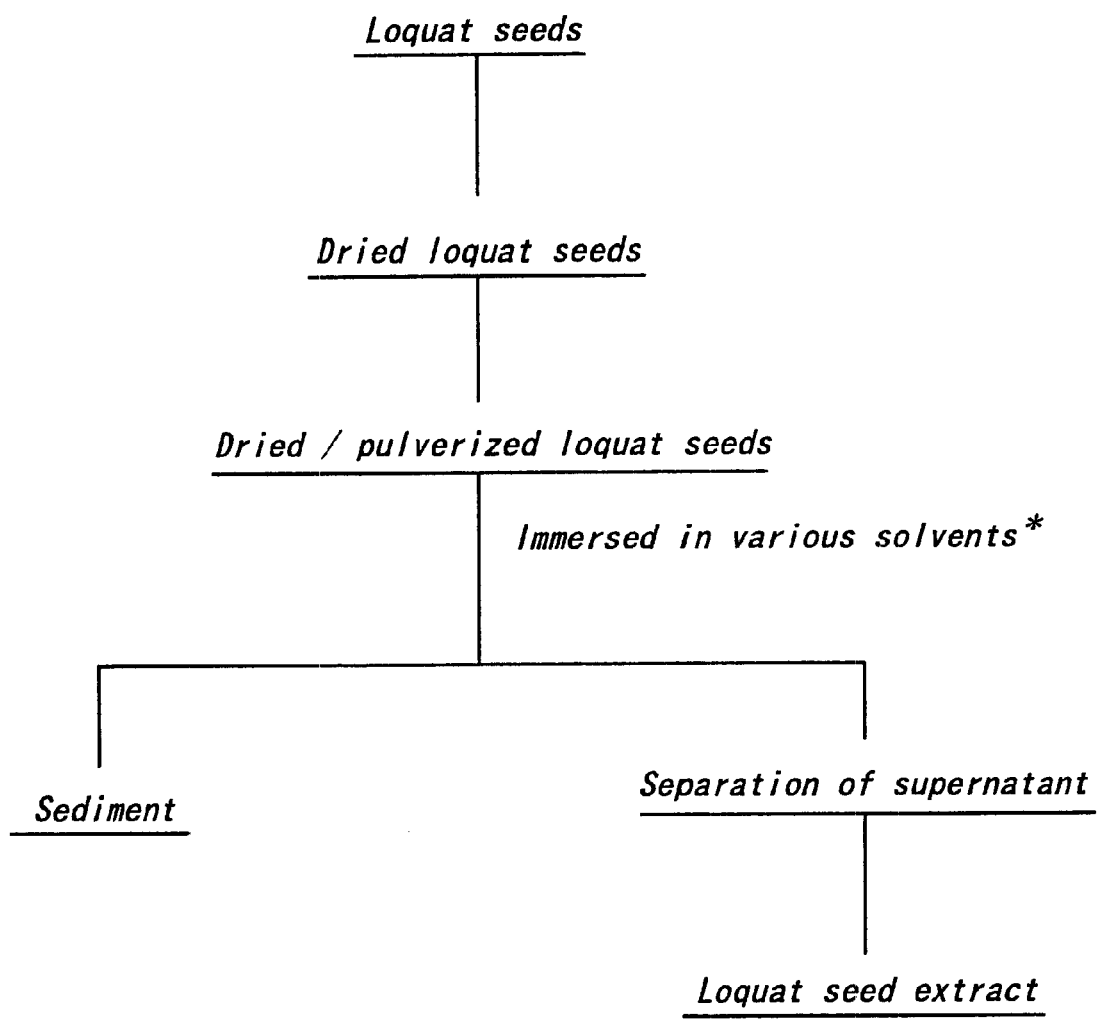
FIG. 1 shows the method for preparing an extract from loquat seeds.

Firstly, the method for preparing an extract from loquat seeds will be described with reference to FIG. 1. FIG. 1 shows the method for preparing an extract from loquat seeds. Loquat seeds are collected. The loquat seeds should be washed as needed, and then dried. The seeds are preferably dried thoroughly. This is in order to uniformly effect the succeeding pulverization.

Next, the loquat seeds are pulverized. The method for pulverization is not limited to any specific one, and may employ any publicly known pulverizing machine such as a ball mill, hammer mill, roller mill, rod mill, sample mill, stamp mill, disintegrator, mortar and pestle, blender with a cooler, etc. However, pulverization with a blender with a cooler is preferred because otherwise heat generated during milling might decompose the composition included in the loquat seeds.

The loquat seeds are pulverized to produce a pulverized material. Then, the grains are immersed in a solvent. The solvent is not limited to any specific one, but any appropriate solvent may be selected according to the desired effect of the resulting extract. The solvent may include any polar or non-polar solvents such as ethanol, methanol, water, hexane, ethyl acetate, chloroform, acetone, etc. However, methanol, ethanol, water or the like is preferred because such a solvent will allow the extraction of an extract which can readily pass through cellular membranes.

Immersion of the extract in the solvent may occur under gentle shaking. The grains may be immersed in various solvents to produce different solutions. The different solutions thus obtained may be stirred according to the condition of the solution, and some solutions may be left unstirred as appropriate. The method of stirring is not limited to any specific one, but stirring may be continuously effected for five to ten days.

Later, the supernatant is separated to produce a loquat seed extract. The supernatant may be allowed to evaporate to dryness as needed. Drying through evaporation may be effected in an evaporator including a water bath kept at 55–88° C. The loquat seed extract thus dried through evaporation can be stored for a long time.

Components of the Loquat Seed Extract

Components contained in a loquat seed are separated according to their properties, through extraction using various solvents different in polarity. Accordingly, the components and their concentrations of a loquat seed extract are different according to the solvent used.

Figure 2:
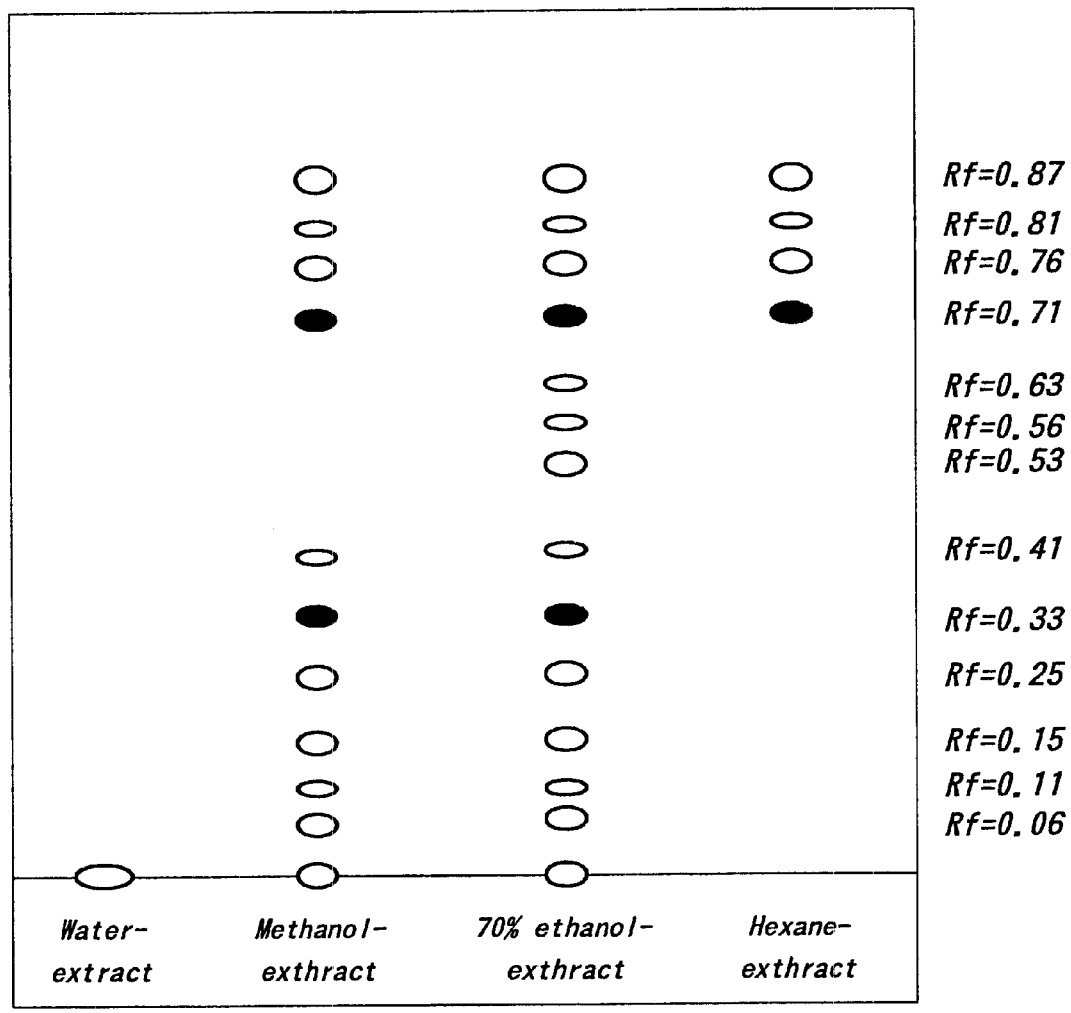
FIG. 2 shows results of thin layer chromatograghy when various solvents were used for extraction.

FIG. 2 shows the thin-layer chromatograms for the components of various loquat seed extracts extracted through different solvents.

According to these thin-layer chromatograms, an extract obtained by using water as the solvent (to be referred to as a water-extract hereinafter) gives only a spot at the original point, and thus it appears the extract contains highly polarized compounds such as proteins, sugars, amygdalin, etc.

An extract obtained by using 70% ethanol (70% ethanol-extract) and that from methanol (methanol-extract) give smaller spots at the original point than does the water-extract, and thus it appears the former two extracts contain smaller amounts of highly polarized compounds such as proteins, sugars, amygdalin, etc.

For the thin layer chromatograms obtained from the 70% ethanol extract and the methanol extract, it was revealed by structural analysis that a compound whose Rf value is 0.63 is linolenic acid; a compound whose Rf value is 0.53 is β-sitosterol; a compound whose Rf value is 0.41 is linoleic acid; and a compound whose Rf value is 0.25 is β-sitosterol monoglycoside. Therefore, the 70% ethanol extract and the methanol extract contain at least the compounds mentioned above.

The extract from hexane (hexane-extract) contains, as revealed by its thin-layer chromatogram, compounds whose Rf values are 0.71 or higher, and thus it appears the hexane-extract contains larger amounts of weakly polarized compounds.

Effective Dose

The composition according to this invention is prepared to contain an effective amount of the loquat seed extract in an appropriate dosage form.

The dose of the composition of this invention obtained from the loquat seed extract may be varied according to the disease condition of a given patient, the severity of the condition, the dosage form, the administration route selected, and the number of doses per day etc.

The appropriate dose of the composition of this invention obtained from the loquat seed extract is at least 375 mg/kg/day for a rat, and is preferably lower than the above when it is applied to a human being, because the sensitivity to the composition is different between the rat and the human being.

The composition may be administered as an orally applicable agent (tablets, capsules, coated tablets, granules, solutions, syrups), as a suppository for rectal administration, or as an injectable agent. Since it will be mainly used for chronically ill patients, it is preferably administered as an orally applicable agent, because oral administration facilitates continuous use over a long period.

The dose may include conventional additives such as a stabilizing agent, a sweetener, a colorant, a perfumer, etc.

Acute Toxicity Test

Carter, J. H. et al. studied the toxicity of amygdalin, one of the components of the loquat seed extract, and reported its lethal dose for rats is 600 mg (Carter, J. H., Mclefferty, M. A., Goldman, F., Biochem. Pharamcol. 29, 301(1980)).

The lethal dose of the loquat seed extract for humans is estimated to be 8060 mg/kg, from the content of amygdalin (7.4%) in the extract.

EXAMPLE

Examples of this invention will be given below, but this invention should not be interpreted as being limited to those examples only.

To investigate the suppression effect of the loquat seed extract on hepatocyte fibrousing, the following study was undertaken: various loquat seed extracts were prepared (FIG. 1); they were orally given to rats which had been treated with dimethylnitrosamine, that is, experimental models of hepatopathy; and to reveal the suppression effects of the extracts on hepatocyte fibrousing, the biochemical activities of some hepatic enzymes (the activities of GOT and GPT), the retinoid content in liver, the content of hydroxyproline occurring in collagen, and the rate of fibrousing were measured, and compared with those from control rats fed on common feed.

Example 1

Preparation of Various Loquat Seed Extracts

Loquat seeds were obtained from the Kochi Municipal Orchard, and were thoroughly sun-dried. They were pulverized with a blender with a cooler (1,000 rpm), and 1,050 g of the grain was immersed in a solvent two times as heavy as the grain. The solvent included 70% ethanol, methanol, water and hexane (2,100 ml). The suspension was continuously stirred with a stirrer (300 rpm), and seven days after immersion of the grain in the solvent, the supernatant was separated. The supernatant was put in an evaporator where it was allowed to evaporate to dryness over a water bath kept at 70° C.

The weight of the extract was 10.4 g (1.0% extraction) when 70% ethanol was used, 9.7 g (0.9% extraction) when methanol was used, 15.7 g (1.5% extraction) when water was used, and 4.5 g (0.4% extraction) when hexane was used.

Example 2

Effects of Various Loquat Seed Extracts on the Biochemical Activities of Hepatic Enzymes of Rats 7-week-old Male Wistar rats had been normally fed for one week to check their healthy condition; to rats which had been found healthy, a single dose of dimethylnitrosamine (40 mg/kg) was intraperitoneally administered, to induce hepatocyte fibrousing.

A test extract was dissolved in water two times as heavy as the extract, to give a test solution. Seven days after the dimethylnitorosamine treatment, the hepatopathic rats were allowed to drink the test solution freely from a drinking bottle. Normal rats were similarly treated.

The content of the extract in the solution was 0.5% for the 70% ethanol-extract, 0.45% for the methanol extract, 0.75% for the water-extract, and 0.2% for the hexane extract, respectively.

Seven days after the loquat seed extract treatment, both the normal rats and the hepatopathic rats were killed, and the activities of glutamate oxaloacetate transaminase (GOT) and glutamate pyruvate transaminase (GPT) in serum were determined with a Vision analyzer (Dynabot).

The results are shown in FIG. 3. The GOT and GPT values of the hepatopathic rats fed on normal feed were far higher than those of the normal rats. The GOT values of the rats fed on the loquat seed extract varied according to what loquat seed extract they were fed. Particularly when the rats were fed on the 70% ethanol or methanol extract, they showed lower levels of GOT than did the hepatopathiic rats fed on normal feed. The same effect was also evident in the rats fed on the water-extract or hexane-extract as compared with the hepatopathiic rats fed on normal feed.

It is likely from the above results of GOT and GPT activities that progression of hepatopathly is successfully suppressed through intake of the loquat seed extract.

Example 3

Effects of Various Loquat Seed Extracts on the Retinoid Content in the Liver of Rats Preparation of hepatopathic rats and administration of various loquat seed extracts to them were conducted in the same manner as in Example 2.

Of the hepatopathic rats fed on normal feed and the hepatopathic rats fed on various loquat seed extracts, the content of retinyl palmitate in liver was determined seven days after the onset of experimental feeding. The liver was excised from the rat; a piece weighing about 0.3 g was sampled from the same site of the liver; 5 ml of chloroform was added to the piece; the mixture, while being cooled with ice, was homogenized with a cell grinding machine (Irad) (10,000 rpm, two minutes) to give a homogenate; the homogenate was then centrifuged (3,500 rpm, 20 minutes); and the underlying layer was separated to serve as a sample. The sample was filtered with a 0.5 $\mu$m membrane filter (Millipore) and the filtrate was used for HPLC analysis.

The analysis condition was as follows.

Equipment: high performance liquid chromatographic machine (Hitachi, L6000)

Detector: UV detector (Hitachi, L3000)

Wavelength of UV for detection: 310 nm

Column: Cosnoseal 5C18 (150×4.6 mm i.d., Nacarai Tesque)

Measurement temperature: room temperature

Mobile phase: tetrahydrofuran vs. methanol at a ratio of (1:3)

Flow rate: 1.0 ml/min

The results are shown in FIG. 4. The hepatic retinoid content was expressed as a percent of the hepatic retinoid content of normal rats determined immediately after the preliminary feeding period. The hepatic retinoid content was markedly low among the hepatopathic rats fed on normal feed as compared with the normal rats. Among the hepatopathic rats treated with various loquat seed extracts, the hepatic retinoid content varied notably. Particularly, the rats treated with the 70% ethanol-, methanol- or water-extract showed a marked increase in the hepatic retinoid content as compared with the hepatopathic rats fed on normal feed. However, the hepatopathic rats treated with the hexane-extract showed a hepatic retinoid content practically the same as that of the normally fed hepatopathic rats.

Example 4

Effects of Various Loquat Seed Extracts on the Hydroxyproline Content in the Liver of Rats Preparation of hepatopathic rats and administration of various loquat seed extracts to them were conducted in the same manner as in Example 2.

The liver was excised from the rat; a piece weighing about 0.3 g was sampled from the same site of the liver; 5 ml of ethanol was added to the piece; the mixture, while being cooled with ice, was homogenized with a cell grinding machine (Irad) (10,000 rpm, two minutes) to give a homogenate; the homogenate was then centrifuged (3,500 rpm, 20 minutes) to give a supernatant; and 1 ml of the supernatant was precisely sampled, and heated at 60° C. for eight hours to dryness. To the residue were added 40 $\mu$l of ethanol, and 80 $\mu$l of 0.1 mol borate-buffered solution to give a solution, to which was added 40 $\mu$l of 100 mmol 4-fluoro-7-nitrobenzofurazan (NBD.F) to serve as a fluorescent labeling agent; and the reaction was allowed to proceed for 15 hours for fluorescent labeling while light was completely shielded off. To the solution was added 840 $\mu$l of 5 mmol hydrochloric acid to arrest the reaction; the resulting solution was centrifuged (3,500 rpm, 20 minutes) to give a supernatant; the supernatant was filtered with a 0.5 $\mu$m membrane filter (Millipore); and the filtrate was used for HPLC analysis.

The analysis condition was as follows.

Equipment: high performance liquid chromatographic machine (Hitachi, L6000)

Detector: fluorescence detector (Hitachi, L7480)

Wavelength of rays for detection: Ex—475 nm, Em—530 nm

Column: YMC pack ODS-AQ (150×6.0 mm i.d.)

Measurement temperature: room temperature

Mobile phase: acetonitrile vs. water (the ratio being gradually shifted from 35:15 to 50:50 over 15 minutes)

Flow rate: 1.0 ml/min

The results are shown in FIG. 5. The hepatic content of hydroxyproline is markedly high among the hepatopathic rats fed on normal feed as compared with the normal rats. Among the rats treated with various loquat seed extracts, the hepatic contents of hydroxyproline varied notably. Particularly, the rats treated with the 70% ethanol-, methanol- or water-extract showed a marked reduction in the hepatic content of hydroxyproline as compared with the hepatopathic rats fed on normal feed. However, the rats treated with the hexane-extract showed a little decrease in the hepatic content of hydroxyproline as compared with that of the normally fed hepatopathic rats.

Example 5

Effects of Various Loquat Seed Extracts on the Hepatocyte Fibrousing of Hepatopathic Rats Preparation of hepatopathic rats and administration of various loquat seed extracts to them were conducted in the same manner as in Example 2.

The rate of hepatocyte fibrousing of the hepatopathic rats which had been treated with various loquat seed extracts was determined as follows. The liver was excised; it was stained by Azan-Mallory staining; the stained preparation was used to give an image; the image was subjected to computer-based image analysis; the area of hepatocyte fibrousing which was stained blue in the image was determined by calculation; and the area was expressed as a ratio relative to the corresponding area of the reference (hepatopathic rats fed on normal feed).

Figure 6:
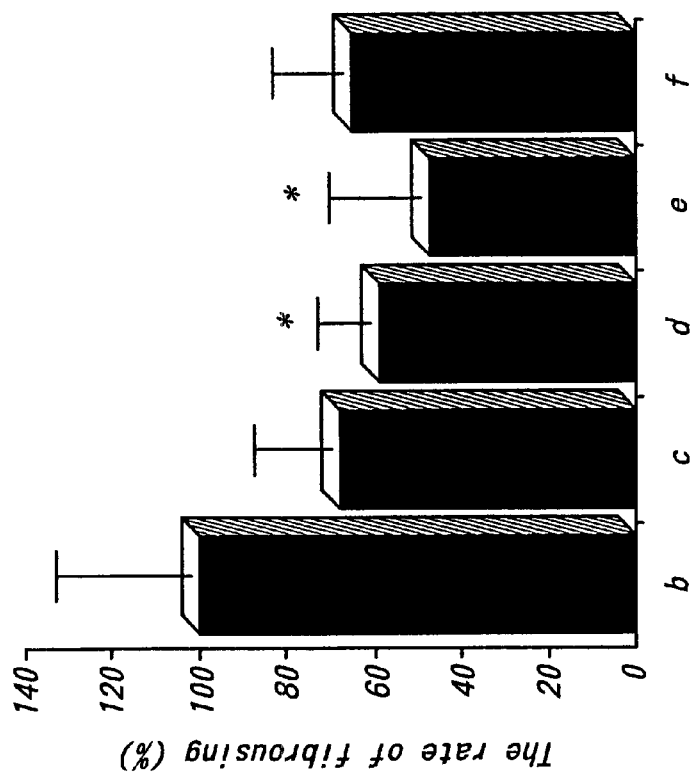
FIG. 6 shows the effect of various loquat seed extracts obtained by means of different solvents on the cellular fibrousing of rats.

The results are shown in FIG. 6. The rate of hepatocyte fibrousing of the rats treated with the loquat seed extract is expressed as a percent relative to the hepatocyte fibrousing seen in the hepatopathic rats fed on normal feed.

The percentage of hepatic fibrousing is markedly low among the hepatopathic rats treated with various loquat seed extracts, as compared with the hepatopathic rats fed on normal feed. Among the hepatopathic rats treated with various loquat seed extracts, the percentage of fibrousings varied notably. Particularly, the rats treated with the 70% ethanol- or methanol-extract showed smaller hepatic fibrousings than did the rats treated with the water- or hexane-extract.

When the loquat seed extract was orally administered to the hepatopathic rats, significant improvement was observed in the biochemical activities of GOT and GPT (see FIG. 3), the hepatic retinoid content (see FIG. 4), the hepatic hydroxyproline content (see FIG. 5), and the hepatocyte cellular fibrousing (see FIG. 6), as compared with the hepatopathic rats fed on normal feed.

The composition of the present invention has an advantage of effectively suppressing the development of cellular fibrousing.

The composition of the present invention contributes not only to the enrichment of medical resources, but also to the expanded use of farming products, the effective use of fruit parts which would otherwise be uselessly discarded, and thus the preservation of natural resources surrounding human society.

The loquat seed extract has an activity to suppress hepatocyte fibrousing in hepatopathic rats: particularly it suppresses the decrease in the hepatic retinoid content or activators of Ito cells, that is, non-parenchymal cells intimately involved in the deposition of fibers in the liver; it reduces the content of hydroxyproline in hepatic collagen, hydroxyproline being an agent to induce hepatic fibrousing; and it improves the percentage of hepatocyte fibrousing. Thus, the loquat seed extract has a characteristic suppression effect on hepatocyte fibrousing.

What is claimed is:

1. A method for preparing an extract from loquat seeds effective for suppressing cellular fibrousing comprising the steps of immersing grains obtained by pulverizing loquat seeds in a solvent, separating a supernatant therefrom, drying the supernatant by evaporation, and forming the extract into a composition suitable for internal administration wherein the solvent is aqueous ethanol.

* * * * *